United States Patent
Nakashima et al.

(10) Patent No.: US 6,929,927 B2
(45) Date of Patent: Aug. 16, 2005

(54) METHOD OF EVALUATING ANTIFUNGAL AGENT

(75) Inventors: Takuji Nakashima, Yokohama (JP); Akira Nozawa, Yokohama (JP); Takao Ito, Yokohama (JP)

(73) Assignee: Pola Chemical Industries Inc., Shizuoka (JP)

(*) Notice: Subject to any disclaimer, the term of this patent is extended or adjusted under 35 U.S.C. 154(b) by 80 days.

(21) Appl. No.: 10/343,586

(22) PCT Filed: Jul. 31, 2001

(86) PCT No.: PCT/JP01/06584

§ 371 (c)(1),
(2), (4) Date: Jan. 31, 2003

(87) PCT Pub. No.: WO02/10440

PCT Pub. Date: Feb. 7, 2002

(65) Prior Publication Data

US 2004/0101866 A1 May 27, 2004

(30) Foreign Application Priority Data

Aug. 1, 2000 (JP) .................................... 2000-232689

(51) Int. Cl.$^7$ ............................................... C12Q 1/18
(52) U.S. Cl. ............................ 435/32; 435/4; 435/7.31; 435/29; 435/30; 435/39; 435/40.51; 435/40.52; 325/243; 325/254.1
(58) Field of Search ............................ 435/4, 7.31, 29, 435/30, 32, 34, 39, 40.51, 40.52, 325, 243, 254.1

(56) References Cited

U.S. PATENT DOCUMENTS 5,789,191 A    8/1998   Mayer et al.

FOREIGN PATENT DOCUMENTS

| EP | 0 504 763 A1 | 9/1992 |
|---|---|---|
| JP | 06-189739 | 7/1994 |

OTHER PUBLICATIONS

Walsh, T.J. et al. 1990. Effects of preventive, early, and late antifungal chemotherapy with fluconazole in different granulocytopenic models of experimental disseminated candidiasis. J. Infect. Dis. 161: 755–760.*

* cited by examiner

Primary Examiner—Jennifer E. Graser
(74) Attorney, Agent, or Firm—Knobbe, Martens, Olson & Bear, LLP

(57) ABSTRACT

A correct viable cell number of a microorganism in a biological tissue is measured by cultivating a fragment of the biological tissue such as skin infected with the microorganism and administered with an antimicrobial agent, in a medium containing a phospholipid, a nonionic surfactant, or both of the phospholipid and the nonionic surfactant.

7 Claims, 1 Drawing Sheet

METHOD OF EVALUATING ANTIFUNGAL AGENT

RELATED APPLICATIONS

This application is the U.S. National Phase under 35 U.S.C. § 371 of International Application PCT/JP 01/06584, filed Jul. 31, 2001, which was published in a language other than English, which claims priority of Japanese Application No. 2000-232689, filed Aug. 1, 2000 Each of the above applications are incorporated herein by reference in their entirety.

TECHNICAL FIELD

The present invention relates to a method for quantitating a microorganism in a biological tissue and a method for evaluating an antimicrobial agent based on the use of the same.

BACKGROUND ART

The medical treatment for the microbial infectious disease is one of the great tasks even in these days in which a large number of antimicrobial drugs have appeared. One of the causes of such a situation is the fact that the sensitivity of the microorganism to the antimicrobial agent always changes due to some affairs such as the acquisition of resistance. Another cause is the fact that certain microorganisms, which are not exterminated by the antimicrobial agent, still exist. As for the causes as described above, the representative cases of the latter involve fungi which cause the dermatophytosis. In the case of the latter, the cause of the almost unsuccessful extermination resides in the fact that there is no evaluation system which makes it possible to screen an agent that is effective upon actual administration to a living body.

The reason, why there is no effective screening system for the antifungal agent as described above, includes the following fact. Usually, the screening for the antifungal agent involves the in vitro screening in which the influence exerted on the growth of fungi is observed on a medium, and the in vivo screening in which an agent is administered to an animal to be infected in vivo, a segment or fragment of a biological tissue therefrom is transplanted to a medium, and the viable cell number of fungi proliferated thereby is counted to estimate the number of fungi surviving in the biological tissue. It is assumed that the in vitro screening is indicative of the antifungal activity of the agent, while the in vivo screening is representative of the effect based on those ranging to the absorption and metabolism characteristics of the living body. However, in the case of the in vivo screening for the antifungal agent or the like, the agent remains at the administration site, and the growth of fungi is inhibited thereby. As a result, the number is counted as if the viable cell number is decreased, in which no appropriate screening is performed for the agent. Any means, which inactivates the agent remaining as described above, has not been known yet until the present time. That is, although it is demanded to realize a means for inactivating the agent remaining in the tissue in order to measure a correct viable cell number in the tissue, such a means has not been obtained yet. Therefore, it is affirmed that this fact impedes the development of effective antifungal agents for the skin.

DISCLOSURE OF THE INVENTION

The present invention has been made taking the foregoing circumstances into consideration. An object of the present invention is to provide a means for measuring a correct viable cell number in a tissue of a living body.

As a result of diligent and repeated investigations and efforts performed by the present inventors in order to seek for a means for measuring a correct viable cell number in a tissue of a living body, it has been found out that the influence of an agent remaining in a tissue can be eliminated by cultivating a segment or fragment of the biological tissue in a medium containing a phospholipid and/or a nonionic surfactant, and thus the invention has been completed. That is, the present invention relates to the technique as specified below.

(1) A method for quantitating a microorganism in a biological tissue, comprising cultivating a fragment of the biological tissue infected with the microorganism and administered with an antimicrobial drug, in a medium containing a phospholipid, a nonionic surfactant, or both of the phospholipid and the nonionic surfactant, and detecting the grown microorganism.

(2) The method for quantitating the microorganism in the biological tissue according to (1), wherein the microorganism is a fungus.

(3) The method for quantitating the microorganism in the biological tissue according to (1) or (2), wherein the biological tissue is skin.

(4) A method for evaluating an antimicrobial agent, comprising administering the antimicrobial agent to a living body infected with a microorganism, taking a fragment of a site of the administration of the agent thereafter, quantitating the microorganism in the fragment by means of the method for quantitating the microorganism as defined in any one of (1) to (3), and using, as an index, a ratio of a microorganism amount obtained when the agent is administered to a microorganism amount obtained when the agent is not administered.

(5) The method for evaluating the antimicrobial agent according to (4), wherein the microorganism is a fungus.

(6) A method for evaluating an antifungal agent, comprising infecting skin of an animal with a fungus, treating the infected skin with the antifungal agent thereafter, quantitating a viable cell number of a site having been treated with the antifungal agent by means of the method for quantitating the microorganism in the biological tissue as defined in (2), and using the viable cell number as an index.

The present invention will be explained in detail below.

The method for quantitating the microorganism in the biological tissue according to the present invention is characterized in that the fragment of the biological tissue, which is infected with the microorganism and which is administered with the antimicrobial agent, is cultivated in the medium containing the phospholipid, the nonionic surfactant, or both of them.

The biological tissue to be used in the present invention is the tissue which is infected with the microorganism and which is treated with the histopathological agent. It is especially preferable to use a tissue in which the agent is stored. The quantitating method of the present invention is useful in such a way that the influence of the agent, which would otherwise affect the situation of the microbial growth as described above, is canceled to count the correct microbial number, for the following reason. That is, the influence of the agent, which would be otherwise exerted on the microorganism, can be canceled by the phospholipid and/or the nonionic surfactant to be used for the quantitating method of the present invention. Even when each of the components is used singly, the component exhibits an activity to inactivate the remaining agent. However, when the phospholipid and the nonionic surfactant are used in combination, a reliable activity is exhibited to inactivate the remaining agent. Therefore, any one of the components can be used to inactivate the agent and quantitate the viable cell number in the biological tissue as well. However, in the present invention, it is especially preferable to use both of them.

Any phospholipid can be used in the present invention without any special limitation provided that the phospholipid is commonly known. Those preferably exemplified may include, for example, lecithin, phosphatidylcholine, phosphatidylinositol, phosphatidylglycerol, phosphatidylethanolamine, phosphatidylserine, phosphatidic acid, and lyso-phospholipids thereof. Among them, lecithin, which is available most easily, is especially preferred. The phospholipid as described above is preferably contained at a content of 0.1 to 10% by weight, and more preferably 0.5 to 5% by weight in total amount with respect to the whole quantity of the medium, for the following reason. That is, if the content is too small, it is impossible to obtain the activity to inactivate the agent in some cases. On the other hand, if the content is too large, then the inactivating activity is not only saturated, but also the phospholipid remains as solid in the medium to disturb the observation in other cases.

Hydrophilic surfactants, each of which has an H.L.B (hydrophilic-lipophilic balance) of not less than 10, are preferably usable as the nonionic surfactant to be used in the quantitating method of the present invention. Especially, it is preferable to use those having a form in which the polyoxyethylene group is added. The average number of moles of added oxyethylene as described above is preferably not less than 6 and not more than 100, and more preferably not less than 10 and not more than 60, for the following reason. That is, if the hydrophilicity is either too high or too low, it is difficult to inactivate the remaining agent when the nonionic surfactant is combined with the phospholipid. Generally, the type of the nonionic surfactant usable in the quantitating method of the present invention may be preferably exemplified as follows on the basis of the form of addition of the polyoxyethylene group. That is, those preferably exemplified may include, for example, polyoxyethylene fatty acid ester, polyoxyethylene alkyl (alkenyl) ether, polyoxyethylene sorbitan fatty acid ester, polyoxyethylene cured castor oil, and polyoxyethylene glyceryl fatty acid ester. Among them, polyoxyethylene sorbitan fatty acid ester is especially preferred, and oleic acid is especially preferred as the fatty acid of such a compound. That is, the nonionic surfactant, which is used most preferably in the quantitating method of the present invention, is polyoxyethylene sorbitan oleic acid ester. Tween 80, which is commercially available from Atlas Chemical Co., may be preferably exemplified as a commercially available product of the nonionic surfactant as described above. In the quantitating method of the present invention, the nonionic surfactant is preferably contained in the medium at a content of 0.01 to 10% by weight, and more preferably 0.1 to 5% by weight in total amount with respect to the whole quantity of the medium, for the following reason. That is, if the content is too small, the effect as described later on is not exhibited in some cases. On the other hand, if the content is too large, then the effect as described later on is saturated, and the growth of fungi or the like is inhibited in other cases. This component acts singly, or it preferably acts together with the phospholipid to exhibit the activity to inactivate the agent remaining in the fragment of the living body.

In the present invention, the biological tissue includes, for example, skin, lungs (respiratory organs), and bowels (digestive organs). However, among them, the skin is preferred.

The microorganism, which is subjected to the quantitation in accordance with the present invention, is not specifically limited provided that the biological tissue is infected with the microorganism. However, microorganisms, which cause the dermatological infection or the skin infectious disease, are preferred, and fungi are especially preferred, because the following tendency is widely known especially in the medical treatment for the dermatophytosis or the dermatomycosis. That is, it is impossible to quantitate any correct viable cell number of fungi surviving in the skin, because the agent is stored in the skin for a long period of time. This consequently causes the difference in efficacy of the agent between the in vivo animal test and the clinical test. The microorganism, to which the present invention is applicable, specifically includes, for example, bacteria such as *Helicobacter pylori*, pathogenic *Escherichia coli*, and *Staphylococcus aureus*, and fungi such as *Trichophyton mentagropytes, Trichophyton rubrum, Candida albicans, Cryptococcus neoformans*, and *Aspergillus fumigatus*.

The fragment of the biological tissue infected with the microorganism may be either a fragment which is taken from a tissue of a living body naturally infected with the microorganism, or a fragment which is taken from a tissue of a living body after infecting the living body with the microorganism by means of a method suitable for the microorganism.

The antimicrobial agent can be evaluated by utilizing the method for quantitating the microorganism in the biological tissue according to the present invention. That is, when the method of the present invention is used, the viable cell number can be quantitated without being affected by the stored agent. Therefore, it is possible to obtain, even in the in vivo test, data which is well correlated with results of the clinical test. Accordingly, it is possible to allow agents having low efficacy to drop out without testing them in the clinical test. It is noted that when such an operation is performed with an experimental infected animal, an efficacy assay test may be constituted. When an infected and medically treated site, which is obtained from an infected person such as a patient, is subjected to the biopsy and the quantitation, it is possible to monitor the medical treatment process. When the biological tissue is taken from an animal or a patient as described above, it is preferable that about 3 to 20 fragments, each of which has a size of about 1–10 mm×1–10 mm, are uniformly taken from a certain site. As for the medium to which the fragment is transplanted, any medium can be used without any special limitation provided that the medium is known as a growth medium for the objective microorganism. In the case of the microorganism such as fungi, those preferably exemplified may include, for example, Sabourand medium, Sabourand modified medium, and RPMI medium.

An embodiment of the method for evaluating the agent is described below.

(1) An experimental animal is infected with the microorganism to prepare an infected animal. In this process, a preferred form of the infection is local infection. In the case of the therapeutic agent for the dermatophytosis, the following procedure may be adopted. That is, the back of the experimental animal such as guinea pig is previously subjected to hair shaving, or bottoms of feet are used in an untreated state. Conidia are picked from a preliminarily cultivated fungus to prepare infectious solutions having uniform concentrations thereof. When the infectious solutions are percutaneously administered, for example, by means of the closed patch, it is possible to prepare an animal model infected with the dermatophytes.

(2) The infected site of the infected animal is treated by administering the agent. Specifically, the treatment method includes, for example, methods of application of the agent solution, oral administration, and intravenous injection.

(3) A fragment of the biological tissue is taken from the agent-administered site of the infected animal. In the case of the skin, the skin is taken out by means of the excision.

(4) The fragment of the biological tissue is inoculated. A medium, which contains the phospholipid, the nonionic surfactant, or both of them, is previously prepared. The fragment of the biological tissue is inoculated to the medium to perform the cultivation. The cultivation is usually performed under a condition including, for example, a temperature suitable for the growth of the microorganism.

(5) After the cultivation, the microbial number is counted, or the size of a formed colony is measured for the microorganism grown from the fragment of the biological tissue to use an obtained result as an index of the number of surviving microbes or the viable cell number. In this process, the following procedure is also advantageous. That is, plates, to which several solutions having different concentrations of conidia are inoculated, are separately prepared to make comparison therewith so that the number of surviving cells itself is estimated. Further, an infected animal, which is not treated with the agent, is prepared to make comparison therewith. Accordingly, it is possible to evaluate the antimicrobial effect of the agent. Specifically, it is possible to use, as an index, the survival rate, i.e., the ratio of a microorganism amount obtained when the agent is administered to a microorganism amount obtained when the agent is not administered.

In a more preferred embodiment, the behavior is confirmed with a medium which contains neither phospholipid nor nonionic surfactant, for the following reason. That is, when such a control is provided for comparison, it is possible to know whether or not the phospholipid and/or the nonionic surfactant adequately inactivates the agent.

BEST MODE FOR CARRYING OUT THE INVENTION

Figure 1:
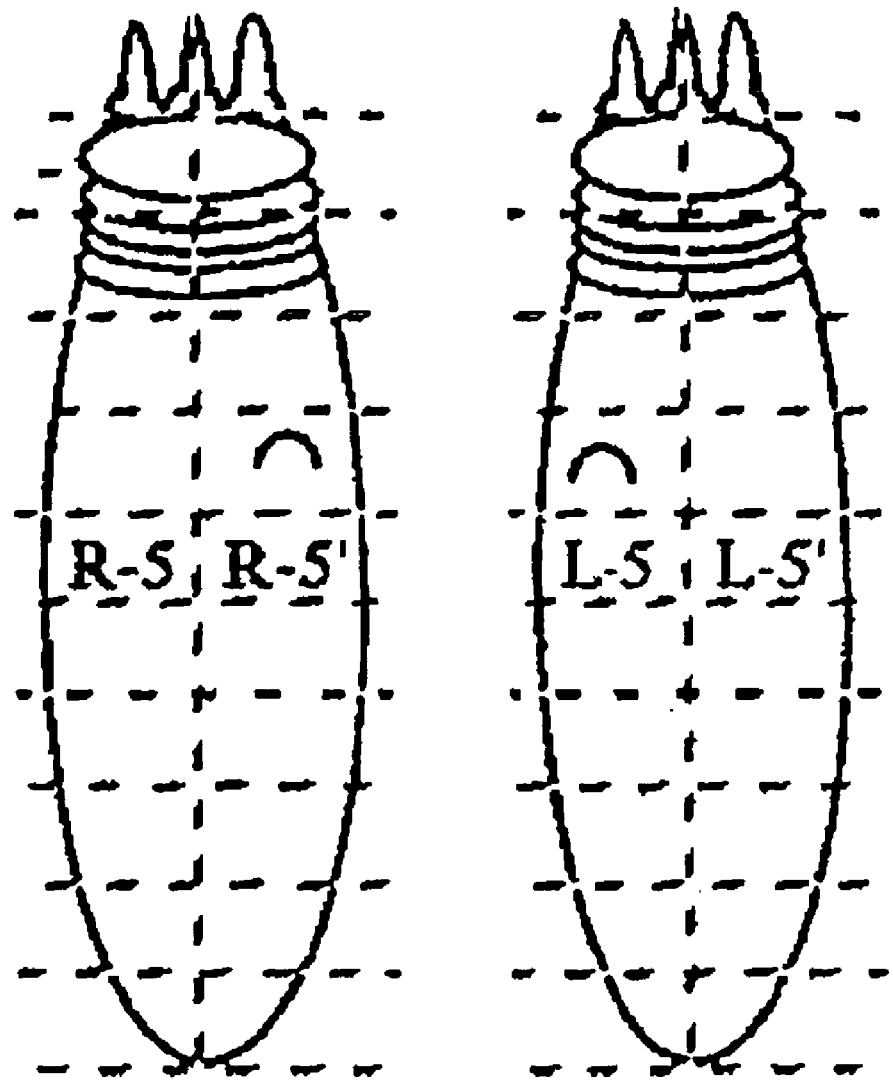
FIG. 1 shows a way of excision of foot skin in Example 2.

The present invention will be more specifically explained below as exemplified by Examples. However, it goes without saying that the present invention is not limited to only Examples.

EXAMPLE 1

MIC (minimum inhibitory concentration) was measured by means of the microdilution method by using 96-well plates to investigate the inactivation of respective agents caused by lecithin and Tween 80. The following four media were used. That is, a Sabouraud liquid medium (SDB) as a base medium, a medium obtained by adding 0.7% Tween 80 to SDB, a medium obtained by adding 1% lecithin to SDB, and a medium obtained by adding 0.7% Tween 80 and 1% lecithin to SDB were used. The following agents were used. That is, lanoconazole, bifonazole, and terbinafine were used.

The following test strain was used. That is, *Trichophyton mentagropytes* TIMM 2789 (available from Institute of Medical Mycology of Teikyo University), which is generally used for the animal infection experiment, was used. The cultivation was performed at 28° C. for 7 days, while the microbial concentration upon the inoculation was about $10^4$ conidia/ml. After the cultivation, it was regarded that MIC ($\mu$g/ml) was represented by the minimum agent concentration of the plate on which no microbial growth was observed by visual observation.

Obtained results are shown in Table 1. According to Table 1, it is clarified that any one of the antifungal agents is inactivated by lecithin as the phospholipid and/or Tween 80 as the nonionic surfactant. Further, it is appreciated that the agents can be inactivated more reliably in a form in which both of the phospholipid and the anionic surfactant are contained, as compared with a form in which each of them is used singly.

TABLE 1

| Additive | Bifonazole | Lanoconazole | Terbinafine |
|----------|------------|--------------|-------------|
| none     | 1.56       | ≦0.005       | ≦0.005      |
| Tween 80 | >25        | 0.312        | 0.312       |
| Lecithin | >25        | 0.078        | 0.078       |

(MIC: $\mu$g/ml)

EXAMPLE 2

The effects of the method for quantitating the microorganism in the biological tissue and the method for evaluating the antifungal agent according to the present invention were confirmed by using an animal model infected with the dermatophytes. Female Hartley guinea pigs were grouped into several groups each including 5 individuals to prepare a foot trichophytosis model by using a method modified by Uchida et al. originating from an original method of Fujita et al. (Fujita, S., and Matsuyama, T., 1978, "Experimental tinea pedis induced by non-abrasive inoculation of *Trichophyton mentagropytes* artbrospores on the plantar part of a guinea pig foot", *J. Med Vet. Mycol.*, 25, 202–213; and Uchida, K. & Yamaguchi, H., 1996, "Preclinical therapeutic evaluation of agents for treating dermatophytosis", *Jpn. J. Med Mycol.*, 37, 199–205). That is, *Trichophyton mentagropytes* TIMM 2789 strain was used to adjust the concentration to $2 \times 10^7$ conidia/ml. Pad-equipped adhesive plasters, in which 100 $\mu$l of the suspension of conidia was allowed to permeate into, lint cotton portions, were fixed to bottoms of feet of right and left hind legs of guinea pigs by using surgical tapes. The adhesive plasters were removed on the 7th day after the fixation. The medical treatment was started on the 28th day after the infection. A commercially available formulation of 1% lanoconazole cream (ASTAT (trade name)), a commercially available formulation of bifonazole (MYCOSPOR), or a commercially available formulation of terbinafine (LAMISIL) was externally applied in an amount of 0.1 g once a day for 3 days. It is noted that the solution used for the test contained polyethylene glycol 400 and ethanol (75:25 vol/vol). 400 and ethanol (75:25 vol/vol).

Skin pieces (1 mm×2 mm) were excised on the 7th day and on the 14th day after the final treatment, while being divided into two vertically and into ten laterally (divided into twenty in total, see FIG. 1). Ten slices of those divided into two vertically were inoculated to a Sabouraud agar medium (SDA) containing 1% lecithin and 0.7% Tween 80, and remaining ten slices were inoculated to SDA to observe the presence or absence of the fungus on both of the media.

(Antibiotics were added to SDA used in accordance with the ordinary method.)

Obtained results are shown in Table 2. According to Table 2, it is appreciated that the agent remaining in the skin behaves as an obstacle for the screening in the in vivo test for the antifungal agent, and that the obstacle can be eliminated by using the quantitating method of the present invention.

TABLE 2

|  | Number of positive cases |
| --- | --- |
| SDA medium only | |
| 7th day after treatment | |
| no treatment control | 10/10 |
| ASTAT cream | 0/10 |
| MYCOSPOR cream | 10/10 |
| LAMISIL cream | 0/10 |
| 14th day after treatment | |
| no treatment control | 10/10 |
| ASTAT cream | 0/10 |
| MYCOSPOR cream | 10/10 |
| LAMISIL cream | 0/10 |
| Added with lecithin and Tween 80 | |
| 7th day after treatment | |
| no treatment control | 10/10 |
| ASTAT cream | 5/10 |
| MYCOSPOR cream | 10/10 |
| LAMISIL cream | 3/10 |
| 14th day after treatment | |
| no treatment control | 10/10 |
| ASTAT cream | 0/10 |
| MYCOSPOR cream | 10/10 |
| LAMISIL cream | 3/10 |

INDUSTRIAL APPLICABILITY

According to the present invention, it is possible to provide the means for measuring the correct viable cell number in a tissue of a living body.

What is claimed is:

1. A method for detecting and/or quantitating a fungus in a mammalian skin tissue, previously treated with an antifungal drug, comprising:

cultivating a fragment of the mammalian skin tissue infected with the fungus and previously treated with an antifungal drug, in a medium containing a phospholipid, a nonionic surfactant, or both the phospholipid and the nonionic surfactant, and detecting and/or quantitating the grown fungus.

2. The method of claim 1, wherein the fungus is selected from the group consisting of *Trichophyton mentagropytes, Trichophyton rubrum, Candida albicans, Cryptococcus neoformans,* and *Aspergillus fumigatus*.

3. The method of claim 2, wherein the fungus is *Trichophyton mentagropytes*.

4. The method of claim 1, wherein the antifungal drug is selected from the group consisting of lanoconazole, bifonazole and terbinafine.

5. The method of claim 1, wherein the phospholipid is lecithin.

6. The method of claim 1, wherein the nonionic surfactant is Tween 80.

7. A method for detecting and/or quantitating a fungus in a mammalian skin tissue which is previously treated with an antifungal drug and in which the antifungal drug remains, comprising:

cultivating a fragment of the mammalian skin tissue infected with the fungus and previously treated with an antifungal drug in which the antifungal drug remains, in a medium containing a phospholipid, a nonionic surfactant, or both the phospholipid and the nonionic surfactant, and detecting and/or quantitating the grown fungus.

* * * * *